United States Patent
Riess et al.

(10) Patent No.: US 6,528,545 B1
(45) Date of Patent: *Mar. 4, 2003

(54) PREPARATIONS COMPRISING A FLUOROCARBON OR HIGHLY FLUORINATED COMPOUND AND A LIPOPHILIC/FLUOROPHILIC ORGANIC COMPOUND, AND THEIR USES

(76) Inventors: Jean G. Riess, Les Giaines, 06950 Falicon (FR); Michele Postel, Les Giaines, 06950 Falicon (FR); Luis Sole-Violan, 791 Chemin de $S^{te}$ Colombe, Immeudle Le Diristello, 06400 Vence (FR); Marie-Pierre Krafft, 3 Quai au Sable, 67000 Strasbourg (FR); Chantal Cornelus, 42 Avenue Junot, 75018 Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/587,169

(22) Filed: Jun. 2, 2000

Related U.S. Application Data (63) Continuation of application No. 08/483,946, filed on Jun. 7, 1995, now Pat. No. 6,113,919, which is a continuation of application No. 07/916,216, filed on Jul. 17, 1992, now abandoned.

(30) Foreign Application Priority Data

Jul. 17, 1991 (FR) .............................. 91 09026

(51) Int. Cl.$^7$ .............................. B01F 3/08; A61K 31/02
(52) U.S. Cl. .......................... 516/56; 516/76; 514/743; 514/746; 514/759; 514/938
(58) Field of Search .................... 516/56, 76; 424/400, 424/450, 70.1, 78.03; 514/759, 832, 833, 938, 743, 746

(56) References Cited

U.S. PATENT DOCUMENTS 3,778,381 A * 12/1973 Rosano et al. ................ 516/67
3,823,091 A * 7/1974 Samejima et al. ............ 516/74

(List continued on next page.)

FOREIGN PATENT DOCUMENTS

EP 0231091 * 7/1986
EP 0231070 * 1/1987

(List continued on next page.)

OTHER PUBLICATIONS

Cecuitti C. et al., New Formulation of blood substitutes: optimization of novel fluorinated microemulsions, Eur. J. Med. Chem. 24:485–492 (1989) Month unknown.*

Naito R. and Yokoyama K., Technical Information, Series No. 5. The Green Cross Corporation, Osaka Japan (1981) month unknown.*

(List continued on next page.)

Primary Examiner—Daniel S. Metzmaier
(74) Attorney, Agent, or Firm—Knobbe Martens Olson & Bear LLP

(57) ABSTRACT

Fluorocarbon emulsions comprising a stabilizing, particle size controlling fluorophilic/hydrophilic compound which can have the formula $$R_F^1\text{—}W\text{—}R_H^1 \qquad (I)$$

wherein
  $R_F^1$ is a linear, branched or cyclic $C_{2-14}$ fluorocarbon group;
  $R_H^1$ is a linear, branched or cyclic $C_{2-18}$ saturated or unsaturated hydrocarbon group; and
  W is absent or is a bivalent species chosen from the group consisting of —O—, —S—, or various fluorinated structures. Use of the fluorophilic/lipophilic compound in the dispersions of the invention provides stable particle size and efficient emulsification. The dispersions of the invention can comprise biologically useful additive and can be used for various purposes, as oxygen carriers, contrast agents, or diagnostic agents.

10 Claims, 9 Drawing Sheets

U.S. PATENT DOCUMENTS

| | | | | |
|---|---|---|---|---|
| 3,989,843 | A | * 11/1976 | Chabet et al. | 514/672 |
| 3,993,581 | A | * 11/1976 | Yokoyama et al. | 516/56 |
| 4,299,728 | A | * 11/1981 | Cormier et al. | 516/67 |
| 4,569,784 | A | * 2/1986 | Moore | 516/99 |
| 4,613,708 | A | * 9/1986 | Reiss et al. | 514/832 |
| 4,859,363 | A | * 8/1989 | Davis et al. | 516/76 |
| 4,895,876 | A | * 1/1990 | Schweighardt et al. | 514/747 |
| 4,927,623 | A | * 5/1990 | Long, Jr. | 514/832 |
| 4,975,468 | A | * 12/1990 | Yiv | 514/759 |
| 4,987,154 | A | * 1/1991 | Long, Jr. | 514/772 |
| 5,185,099 | A | * 2/1993 | Delpuech et al. | 516/76 |
| 5,628,930 | A | * 5/1997 | Weers et al. | 514/743 |
| 5,635,538 | A | * 6/1997 | Weers et al. | 516/56 |

FOREIGN PATENT DOCUMENTS

| | | | |
|---|---|---|---|
| EP | 0255443 | * | 7/1987 |
| EP | 0311473 | * | 9/1988 |
| EP | 0196776 | * | 10/1991 |
| FR | 2515198 | * | 10/1981 |
| WO | 84/00686 | * | 3/1984 |
| WO | 89/10118 | * | 11/1989 |
| WO | 90/15807 | * | 12/1990 |
| WO | 9104664 | | 4/1991 |
| WO | 91/00110 | * | 10/1991 |

OTHER PUBLICATIONS

Naito R and Yokoyama K., Technical Information Series No. 7, The Green Cross Corporation, Osaka, Japan (1981) onth unknown.*

Rabolt, J.F. et al., Structural Studies of semifluorinated n–alkanes:(1). Macromolecules, 17(12):2786–2794 (1984) month unknown.*

Riess, J.G., Hemocompatible materials and devices: prospectives towards . . . Chapter 14 in Blood Compatible Materials and Devices, C.P. Sharma and M Scycker eds. Technomics Publ. Co., Lancaster, PA (1991) month unknown.*

Riess, J.G., Fluorocarbon–based in vivo oxygen transport and delivery systems., Vox Sang. 61:225–239 (1991) month unknown.*

Riess, J.G., Fluorocarbon emulsions for in vivo oxygen delivery and decisive . . . Comptes Rendus du 2e'me Congre's Mondial des Agents de Surface (Paris, France may, 1988), ASPA 4:256–263.*

Shaffer, G.W., et al., Photoisomerism of Nopinone, J. Org. Chem. 37:25–29 (1972) month unknown.*

Twieg, R., et al., Synthesis and characterization of perfluoroalkylalkanes (PFAA) as models for semiflexible polymers., Polym. Prepr. 25(1):154–155 (1984) month unknown.*

Walborsky, H.M., et al., Asymmetric Synthesis of (+)–bicyclo. [2.2.2]–octanol–2., J. Org. Chem. 27:2261 (1962) month unknown.*

Reuter et al., "Preparation, Characterization and Properties of New Fluorosurfactants for In Vivo Application", J. of Fluorine Chem. 54(1–3):C61 (1981) month unknown.*

Riess et al., "Design Synthesis and Emulsifying Properties of New Perfluoroalkylated Phosphatidylcholines", J. of Fluorine Chem., 54(1–3):B41 (1981) month unknown.*

Schulze et al., Comparative Study of N–Containing Fluorosurfactants, J. of Fluorine Chem. 54(1–3):B10 (1981) month unknown.*

Serratrice et al., "Co–Solubilisation de Fluorocarbures et d'eau en Presence de Nouveaux Tensioactifs Non Ioniques Fluores", J. Chem. Phys. 87:1969–1980 (1990) month unknown.*

Napoli et al *Experimental Surface Activity Measurements of Some Fluorinated Compounds in a Non–Aqueous Medium* J. Fluorine Chemistry 51(1) pp 103–115 (1991). Month unknown.

* cited by examiner

PREPARATIONS COMPRISING A FLUOROCARBON OR HIGHLY FLUORINATED COMPOUND AND A LIPOPHILIC/FLUOROPHILIC ORGANIC COMPOUND, AND THEIR USES

This application is a continuation of application Ser. No. 08/483,946, filed Jun. 7, 1995, now U.S. Pat. No. 6,113,919, which is a continuation of application Ser. No. 07/916,216, filed Jul. 17, 1992, now abandoned, wich claims priority to French application No. 91-09026 which was filed Jul. 17, 1991.

The present invention relates to formulations comprising highly fluorinated or perfluorinated compounds, referred to generally as fluorocarbons. It relates particularly to fluorocarbon emulsion formulations that form emulsions having superior emulsion stability and controlled particle sizes.

BACKGROUND OF THE INVENTION

Fluorocarbon compounds and their formulations have numerous applications in human and veterinary medicine as therapeutic and diagnostic agents. Fluorocarbons have many potential applications in the biomedical field, as blood substitutes, or more generally, as carriers in applications wherein oxygen must be supplied to organs and tissues, for example, in the treatment of cardio- and cerebrovascular disease, angioplasty, in organ preservation and in cancer therapy. Fluorocarbon formulations are also useful in diagnostic procedures, for example as contrast agents, and in the field of veterinary therapy (Riess, J. G., *Hemocompatible Materials and Devices: Prospectives Towards the 21st Century*, Technomics Publ. Co, Lancaster, Pa, USA, Chap 14 (1991); *Vox Sanquinis.*, Vol. 61:225–239 (1991). One commercial biomedical fluorocarbon emulsion, Fluosol®, (Green Cross Corp., Osaka, Japan), is presently used, for example, as an oxygen carrier to oxygenate the myocardium during percutaneous transluminal coronary angioplasty (R. Naito, K. Yokoyama, Technical Information, Series n° 5 and 7, 1981).

The dispersed phase of fluorocarbon emulsions must have a stable particle size to be suitable for biomedical use. One of the drawbacks of the Fluosol emulsion is its low stability; the particle size of fluorocarbon emulsions such as Fluosol® can be maintained only if they are transported and stored in the frozen state. The frozen emulsions are then defrosted and mixed with two annex solutions before use. These storage requirements seriously limit the field of application of Fluosol. Although more stable fluorocarbon emulsions are being developed (Oxygent® and Imagent®, Alliance Pharmaceutical Corp., San Diego, Calif.), it is desirable to have fluorocarbon emulsions that are stable enough to store for long periods without refrigeration. Such storage stability would extend the use of fluorocarbons beyond medical facilities in order to meet, for example, the requirements of the army and civil defense. It is also desirable to control particle sizes to adapt the emulsion characteristics to specific applications.

Fluorocarbons are oily substances that are immiscible with water, and therefore fluorocarbon-in-water emulsions, such as Fluosol® and Oxygent®, are presently prepared using lecithins and/or poloxamers of the Pluronic F-68® type as surfactants to disperse the fluorocarbon and stabilize the emulsion. Surfactants are commonly amphiphilic compounds having a hydrophobic end region and a hydrophilic end region. Lecithins have a hydrophobic end region comprising a hydrocarbon groups which have a low affinity for fluorocarbons. It is desirable to improve the affinity of the surfactant film for the fluorocarbon phase and to reduce the interfacial tension between the fluorocarbon and aqueous phases. (Riess, J.G., Comptes Rendus du 2ᵉmeCongrès Mondial des Agents de Surface (Paris, May 1988), ASPA 4:256–263 (1988)).

Several strategies can be employed to overcome this disadvantage:of the emulsifying surfactants described. One approach is to develop more effective surfactants, for example, those having a hydrophobic end which is fluorophilic, for use in the preparation of classic emulsions. Efforts in this direction have led to new fluorinated surfactants such as those described in the documents EP-A- 0 255 443, EP-A-A 0 311 473 and WO 90/15807.

Another strategy is to prepare microemulsions, i.e., preparations of compounds which organize themselves spontaneously into dispersed systems (H. L. Rosano and W. E. Gerbacia, U.S. Pat. No. 3,778,381, Dec. 11, 1973; and G. Mathis, J. J. Delpuech, FR-A-2 515 198, 3.29.1983). In an example of a microemulsion described by Cecutti et al., *Eur. J. Med. Chem.*, 24, 485–492 (1989), the dispersed phase is itself totally constituted of mixed hydrocarbon/fluorocarbon molecules. However, this strategy is not generally applicable to fluorocarbons, particularly those of the examples described in the present invention. Moreover, it is still totally uncertain whether the intravenous administration of microemulsions is safe. To our knowledge, no example of such administration exists in human medicine, whereas the classical emulsions, such as the lipidic emulsions for parenteral nutrition are abundantly used.

It would be advantageous to be able to emulsify any fluorocarbon chosen solely on the basis of its own advantageous properties and its efficacy, without regard to the problem of emulsification. For example, it would be advantageous to be able to prepare stable emulsions of perfluorooctyl bromide (PFOB, Perflubron®, Alliance Pharmaceutical Corp., La Jolla, Calif.) on account of its radiopacity, and of its potential as a contrast agent in diagnostics. It would also be advantageous to set the particle size in the emulsion at a value chosen a priori.

SUMMARY OF THE INVENTION

The invention comprises preparations of dispersions, emulsions, and gels comprising a highly fluorinated compound or fluorocarbon, a surfactant, a lipophilic/fluorophilic organic compound, and an aqueous phase, methods of manufacturing the preparations, and their uses. The preparations of the invention comprise an amphiphilic organic fluorophilic-lipophilic compound of the formula $R_F^1$—W—$R_H^1$ wherein $R_F^1$ is a fluorinated hydrocarbon radical and $R_H^1$ is a hydrocarbon radical as defined herein and W is absent or is —O—, —S—, or a hydrocarbon group or a hydrocarbon group having fluorinated regions as defined herein.

The lipophilic/fluorophilic compound of the invention can be a branched chain structure comprising hydrocarbon groups and fluorinated hydrocarbon groups, as for example, formulas (II) and (III). The fluorinated hydrocarbon groups of the compound can be further substituted by Br and Cl in addition to F. In a preferred embodiment of the invention, the lipophilic/fluorophilic compound is of the formula wherein $t_1=2$ to 11, $t_2=0$ or 1 to 6 and $y=1$ to 15.

The lipophilic/fluorophilic compound is advantageously constituted of one or more essentially hydrocarbon fragments of the formula (II) described below and one or more highly fluorinated fragments, typical examples of such compounds being the molecules $CF_3(CF_2)_x(CH_2)_yCH_3$ or $$CF_3(CF_2)_{t1}-(CH_2)_{t2}-CH=CH-(CH_2)_y-CH_3$$

The preparations of the invention further comprise a surfactant selected from a lecithin, a lecithin analog, or the perfluoroalkylated surfactants. The proportions of the components of the preparations are preferably from about 10 to 130% weight/volume of a fluorocarbon-containing phase; from 0.05 to 10% weight/volume of a surfactant; and from about 0.1 to 50% weight/volume of the fluorophilic/lipophilic compound in a suitable aqueous phase.

The emulsions can further comprise any additive suitable to enhance the purpose of the formulation, such as mineral salts, buffers, pharmaceuticals, nutrients, or diagnostic agents. The fluorocarbon can be any suitable fluorocarbon compound, but preferably those molecular species disclosed herein.

The preparations of the invention are prepared by adding an appropriate quantity of the fluorophilic/lipophilic compound to the fluorocarbon or to the aqueous phase prior to emulsification to achieve the desired final concentration of the compound in the emulsion. The addition of the fluorophilic/lipophilic compound acts to bring the emulsion particles to a desired size more rapidly, and to stabilize the emulsion against changes in particle size on storage. The stabilizing effect is relatively independent of storage temperature.

The preparations can have various forms: dispersions, emulsions or gels, and can be used for various purposes, as oxygen carriers, drug carriers or as contrast agents.

BRIEF DESCRIPTION OF THE DRAWINGS

☆: Change in mean particle diameter d without F8H8E.

★: change in mean particle diameter d with F8H8E.

Δ: percent of particles <0.12 μm diameter with F8H8E.

☐: percent of particles <0.12 μm diameter without F8H8E.

▲: particles >0.6 μm without F8H8E.

■: percent of particles >0.6 μm with F8H8E.

DETAILED DESCRIPTION OF THE INVENTION

The present invention is directed to forming substantially stable dispersed preparations, whether in the form of dispersions, emulsions or gels, through the use of additives that improve the stability of emulsions wherein the hydrophobic or oily phase of the preparation contains a highly fluorinated compound or a perfluorocarbon compound, prepared using classical surfactants. The additives also provide a tight control of particle size.

Definitions:

Fluorocarbon is an analogue of a hydrocarbon which is highly fluorinated, having at least half of the hydrogen atoms replaced by fluorine atoms, or perfluorinated, having all of the hydrogen atoms replaced by fluorine atoms.

Hydrocarbon radical, hereinafter $R_H$, is a linear, branched or cyclic, saturated, monounsaturated or polyunsaturated hydrocarbon group, wherein the unsaturated bonds are ethylenic or acetylenic. In these groups, one or more atoms of the carbon chain can be replaced by other bivalent species, such as O or S.

Fluorinated hydrocarbon radical, hereinafter $R_F$, is a linear, branched, or cyclic hydrocarbon group which is highly fluorinated, having at least half of the hydrogen atoms replaced by fluorine atoms, or perfluorinated, having all of the hydrogen atoms replaced by fluorine atoms. Some of the fluorine atoms can be replaced by Cl and Br; one or more atoms of the carbon chain can be replaced by other bivalent species, such as O or S.

Fluorophilic/lipophilic compound is an amphiphilic molecule having a fluorinated hydrocarbon structure, as defined above, linked to a substantially hydrocarbon structure, as defined above, of the conventional composition of carbon and hydrogen.

Preparations according to the invention accordingly comprise (1) an oily or hydrophobic phase comprising at least one highly fluorinated compound or perfluorocarbon; (2) a continuous phase; (3) at least one conventional surfactant; and (4) an amphiphilic organic compound having a fluorophilic region comprising a fluorinated hydrocarbon radical and a lipophilic region, comprising a hydrocarbon radical.

According to a preferred embodiment of the invention, the dispersed preparation is of the oil-in-water type wherein the hydrophobic phase containing the fluorocarbon or highly fluorinated compound is dispersed in a continuous aqueous phase.

According to one embodiment of the invention, the organic fluorophilic-lipophilic compound is of the formula:

wherein $R_F^1$ is a linear, branched or cyclic $C_{2-14}$ fluorocarbon group;

$R_H$ is a linear, branched or cyclic $C_{1-18}$ saturated or unsaturated hydrocarbon group; and W is absent or is a bivalent species chosen from the group consisting of —O—, —S—, or is of the formula:

wherein $X^1$, $X^2$ and $X^3$ are absent or are independently selected from the group consisting of —O—, or —S—;

$R_F^2$ is a fluorocarbon independently selected from the group defined for $R_F^1$;

$R_H^2$ is a hydrocarbon independently selected from the group defined for $R_H^1$; and $R^2$ is a fluorocarbon or a hydrocarbon independently selected from the group defined for $R_F^1$ or $R_H^1$; and p and q are independently 1–10.

In yet other embodiments, the carbon chain of the $R_H^1$ or $R_H^2$ region of the fluorophilic-lipophilic compound can contain a substituent selected from the group consisting of —O— and —S—, wherein $R^1$ is a linear or branched $C_{1-12}$ alkyl group.

According to another embodiment of the invention, the organic fluorophilic/lipophilic compound is of the formula:

wherein

X4 is —O—, —S— or —S—S—; and a1 and a2 are independently from 0 to 11.

According to yet another embodiment of the invention, the organic fluorophilic/lipophilic compound is of the formula:

wherein $X^5$ is —O—, —S—, or —S—S—;

p and q are independently from 1 to 10;

$R_F^1$ and $R_F^2$ are independently selected from a group of perfluoroalkylated radicals having from 2 to 10 carbon atoms, and $R_H^3$ is selected from the group of hydrocarbon radicals having from 2 to 16 carbon atoms.

The preparations of the invention, whether in the form of a dispersion, an emulsion or a gel, comprise a substantially aqueous phase which is not miscible with the oily phase, as well as at least one natural or synthetic surfactant, in particular a hydrophilic-lipophilic surfactant such as those generally used for the preparation of dispersions, emulsions or gels. Examples of such surfactants are lecithins, perfluoralkylated surfactants, and their mixtures.

The fluorocarbon dispersions to which the compositions of the invention are directed are distinct from the conventional oil-in-water emulsions in their physical complexity. Oil particles are held dispersed in conventional emulsions and dispersions by virtue of a surfactant molecule, which is a molecule having an amphipathic structure comprising a lipophilic region, such as a hydrocarbon structure which has affinity for fatty substances which are also mainly hydrocarbons, and also comprising a hydrophilic or polar region, which has affinity for the polar water molecules of the aqueous phase. Without a surfactant, the water immiscible oil phase would separate rapidly from the aqueous phase in the presence of water. The surfactant acts to lower the interfacial tension between the aqueous phase and the lipid phase and to build an interfacial film around each droplet of the dispersed phase, which stabilizes the emulsion.

Fluorocarbons are heavy water immiscible liquids which are like oily substances except that they are neither hydrophilic nor lipophilic. Thus the interfacial tension between fluorocarbon liquids and an aqueous phase cannot be effectively reduced by conventional surfactants. However, an amphiphilic system that is analogous to a conventional lipophilic/hydrophilic surfactant, but having fluorophilic/hydrophilic regions is preferable. This system is structured, according to the present invention by using, in combination, paired molecules comprising a conventional surfactant and a fluorophilic/lipophilic molecule, which act together in association to reduce the interfacial tension and stabilize the dispersion. In this case, the addition of compound $R_F^1$—W—$R_H^1$ which bears both a lipophilic hydrogenated part ($R_H^1$) and a fluorophilic fluorinated part ($R_F^1$) facilitates the adhesion of the aqueous phase to the oily, fluorocarbon-based phase of the dispersion, emulsion or gel, by interaction of this compound with the lipophilic part of the hydrophilic-lipophilic surfactant.

In such preparations, indeed, the conventional hydrophilic-lipophilic surfactant on the one hand, and the $R_F^1$—W—$R_H^1$ compound on the other hand, constitute two distinct types of molecules whose contributions are complementary and assure to the conventional surfactant a good aqueous/lipidic membrane phase interaction, and the latter ($R_F^1$—W—$R_H^1$ compound) a good lipidic membrane/fluorbcarbon interaction.

This can be illustrated schematically in terms of synergistic surfactant effects as follows:

| Surfactant Effect | Water | | Fluorocarbon |
|---|---|---|---|
| (1) | hydrophilic | <--> lipophilic | |
| (2) | | lipophilic | <--> fluorophilic |

Contribution (1) is furnished by the hydrophilic-lipophilic surfactant and contribution (2) by the lipophilic-fluorophilic compound, for example of formula $R_F^1$—W—$R_H^1$, in conformity with the invention.

The $R_F^1$—W—$R_H^1$ compounds are generally very unreactive and nontoxic, and thus suitable for biomedical applications.

Their use in the formulations of the invention eliminates the need to use other surfactants whose biocompatibility must be tested. The desired effect can also be obtained by using small quantities of $R_F^1$—W—$R_H^1$.

According to the invention, the fluorophilic chain of compound $R_F^1$—W—$R_H^1$ which corresponds to $R_F^1$, and in some cases to $R_F^2$, is a straight or branched fluorinated hydrocarbon radical, of 2 to 14 carbon atoms, which may bear oxygen atoms and/or other substituents for example, Cl.

Examples of fluorinated radicals that can be used are:

$CF_3(CF_2)_t$— wherein t=1 to 11;
$(CF_3)_2CF(CF_2)_v$— wherein v=0 to 8;
$CF_3(CF_2CF(CF_3))_w$— wherein w=1 to 4;
$C_2F_5(CF_2CF(CF_3))_w$— wherein w=1 to 4;
$(CF_3)_2(CFCF_2CF(CF_3))_w$— wherein w=1 to 3; and wherein x=1 to 6; and $R_F^1$ and $R_F^2$ are. independently chosen from the group consisting of $CF_3$—, $C_2F_5$—, n-$C_3F_7$—, n-$C_4F_9$, and $CF_3CF_2CF(CF_3)$—; or $R_F^1$ and $R_F^2$ together form a bivalent radical chosen from the group consisting of:
—$CF_2$ $(CF_2)_2CF_2$—
—$CF_2(CF_2)_3CF_2$—; and
—$CF_3CF_2O$—$(CF_2CF_2O)_y$—$CF_2$—
wherein y=0 to 3; and
$CF_3(CF_2)_2O$—$(CF(CF_3))(CF_2O)_y$—$CF(CF_3)$—
wherein y=0 to 2.

Among the fluorinated radicals corresponding to the above formulas, the radical of formula $CF_3(CF_2)_t$, in which t is a whole number from 1 to 11, and preferably from 3 to 9, are particularly useful.

According to the invention, the lipophilic part of compound $R_F^1$—W—$R_H^1$, represented by $R_H^1$ and possibly $R_H^2$ is a linear, branched or cyclic, saturated or unsaturated, hydrocarbon radical, of from 1 to 18 carbon atoms, which may bear in its chain 1 or several groups.

Examples of radicals from among which $R_H^1$ and $R_H^2$ can be chosen are:

(a) $CH_3$—$(CH_2)_{y1}$— wherein $y_1$=1 to 17;
(b) $CH_3(CH_2)_{y2}(CH=CH)q(CH_2)_{y3}$—
$CH_3(CH_2)_{y2}$—$CON(R_H^1)$—$(CH_2)_{y3}$—
$CH_3(CH_2)_{y2}$—S—$(CH_2)_{y3}$—
and $CH_3(CH_2)_{y2}$—$N(R_H^1)$—$(CH_2)_{y3}$—
wherein $Y_2$ and $y_3$ are independently 1 to 16,
q=0 or 1, and $R_H^1$ is as defined above;
(c) $CH_3(CH_2$—$CH_2$—$O)_{y4}$—$CH_2$ wherein y4=1 to 8; and
(d) $CH_3(CH(CH_3)CH_2O)_{y5}$—CH—$CH_3$ wherein y5=1 to 5.

According to a particularly preferred embodiment of the invention, in compound $R_F^1$—W—$R_H^1$:

$R_H^1$ is $R^4$—CH=CH—$(CH_2)_p$— wherein $R^4$ is a linear alkylated radical of 2 to 12 carbon atoms, and p is equal to 0 or is a whole number from 1 to 8, and W is a single bond.

Examples of compounds $R_F^1$—W—$R_H^1$ that can be used in this embodiment of the invention are:

in which $t_1$ is a whole number from 2 to 11, $t_2$ is a whole number from 0 to 6 and $_{y6}$ is a whole number from 1 to 15.

These compounds can be prepared by classical procedures, for example, by addition of a perfluoroalkylated iodide of formula $CF_3$—$(CH_2)_{t1}(CH_2)_{t2}$ to an olefin of formula $CH_3$—$(CH_2)_{y6}$—CH=$CH_2$, followed by dehydroiodation (J. Org. Chem. 27:2261 (1962) and J. Org. Chem. 37:24–29 (1972)).

Examples of compounds corresponding to the above formula are those in which $t_1$=3,5 or 7, $t_2$=0, and $_{y6}$=3, 5, 7 or 9.

These compounds are of much interest, as they are of low toxicity. Intraperitoneal injection of such compounds into mice at a dose of 25 mL/kg body weight showed no toxicity. Intravascular injection of such compounds in the form of an emulsion (F6H10E/EYP 25/6% w/v) into rats is well tolerated by the animals (no death resulted among 33 animals given a 15 ml/kg body weight dose). The half retention time in liver for F6H10E is about 24 days (to be compared with 65 days for perfluorotripropylamine).

According to a preferred embodiment of the invention, the $R_H^1$ moiety of compound $R_F^1$—W—$R_H^1$, is a linear alkylated radical of 4 to 12 carbon atoms, and W is a single bond.

Examples, of compounds $R_F^1$—W—$R_H^1$ that are useful in this second embodiment of the invention are the semi-fluorinated n-alkanes which can be prepared by the procedures described by Rabolt et al. in *Macromolecules*, 17(12), 2786–2794 (1984) or by Twieg et al. in *Polym. Prep.*, 25, 154–5 (1984).

According to other embodiments of the invention, the $R_H^1$ moiety of the compound $R_F^1$—W—$R_H^1$ is an alkylated, linear radical of C4 to C12, and W is a group of one of the following formulas:

in which $X^1$, $X^2$, $X^3$, $R_H^2$, $R_F^2$ and $R^2$ are defined as above.

In these different embodiments of the invention, $R_F^1$ is preferably a perfluorinated linear radical of formula $CF_3(CF_2)_t$, and t is a whole number from 1 to 11.

Compounds $R_F^1$—W—$R_H^1$ which correspond to these different embodiments of the invention can be prepared by classical procedures. In the preparations of the invention, the fluorocarbons constituting the oily phase can be linear or cyclic compounds, with molecular weights preferably from 400 to 700, and they can be chosen, for example, from among perfluorodecalin, 1,2-bis(F-alkyl)ethenes, 1,2-bis(F-butyl) ethenes, 1-F-isopropyl, 2-F-hexylethenes and 1,2-bis (F-hexyl) ethenes, perfluoromethyldecalins, perfluorodimethyldecalins, perfluoromethyl-, and dimethyladamantanes, perfluoromethyl-dimethyl- and trimethylbicyclo (3,3,1) nonanes and their homologs, perfluoroperhydrophenanthrene, ethers of formulae: $(CF_3)_2CFO(CF_2CF_2)_2OCF(CF_3)_2$, $(CF_3)_2CFO(CF_2CF_2)_3OCF(CF_3)_2$, $(CF_3)_2CFO(CF_2CF_2)_2F$, $(CF_3)_2CFO(CF_2CF_2)_3F$, $F[CF(CF_3) CF_2O]_2CHFCF_3$, $[CF_3CF_2CF_2(CF_2)u]_2O$ with u=1, 3 or 5, amines $N(C_3F_7)_3$, $N(C_4F_9)_3$, $N(C_5F_{11})_3$, perfluoro-N-methylperhydroquinolines and perfluoro-N-methylperhydroisoquinolines, perfluoroalkyl hydrides such as $C_6F_{13}H$, $C_8F_{17}H$, $C_8F_{16}H_2$ and the halogenated derivatives $C_6F_{13}Br$, $C_8F_{17}Br$ (perflubron), $C_6F_{13}CBr_2CH_2Br$, 1-bromo 4-perfluoroisopropyl cyclohexane, $C_8F_{16}Br_2$, $CF_3O(CF_2CF_2O)_uCF_2CH_2OH$ with u=2 or 3. These compounds can be used alone or in mixtures.

In preparations in the form of dispersions, emulsions or gels, the surfactants used generally comprise a hydrophilic part and a hydrophobic part, and can consist of fluorinated or non-fluorinated surfactants. Preferably, classical surfactants are used, such as those usually employed in preparations for biomedical use, for example, phospholipids and poloxamers such as copolymers of polyoxyethylene-polyoxypropylene type, such as Pluronic F-68®, and their mixtures.

When the preparation of the invention is in the form of a dispersion, an emulsion or a gel and comprises an aqueous phase and at least one surfactant, its composition is generally in the following ranges:

from 10 to 130% in weight/volume of oily phase;
from 0.1 to 10% in weight/volume of surfactant(s); and
from 0.01 to 50% in weight/volume of lipophilic-fluorophilic organic compound(s), the rest being constituted by the aqueous phase.

In a preferred embodiment, the composition contains from 0.01% to 10% of a lipophilic/fluorophilic organic compound or a mixture of such compounds.

The preparations in the form of emulsions can be made by the classical procedures generally used to prepare emulsions. For example, such preparations can be made by dispersing the surfactant(s) and the $R_F^1$—W—$R_H^1$ compounds in an aqueous phase which may contain other additives, then adding the oily phase to this dispersion and emulsifying the whole mixture by classical techniques. Appropriate techniques are described, for example, in EP-A-0 231 070 and EP-A- 307 087. Compound $R_F$—W—$R_H^1$ can also be added to the oily phase before mixing the two phases.

Figure 1:
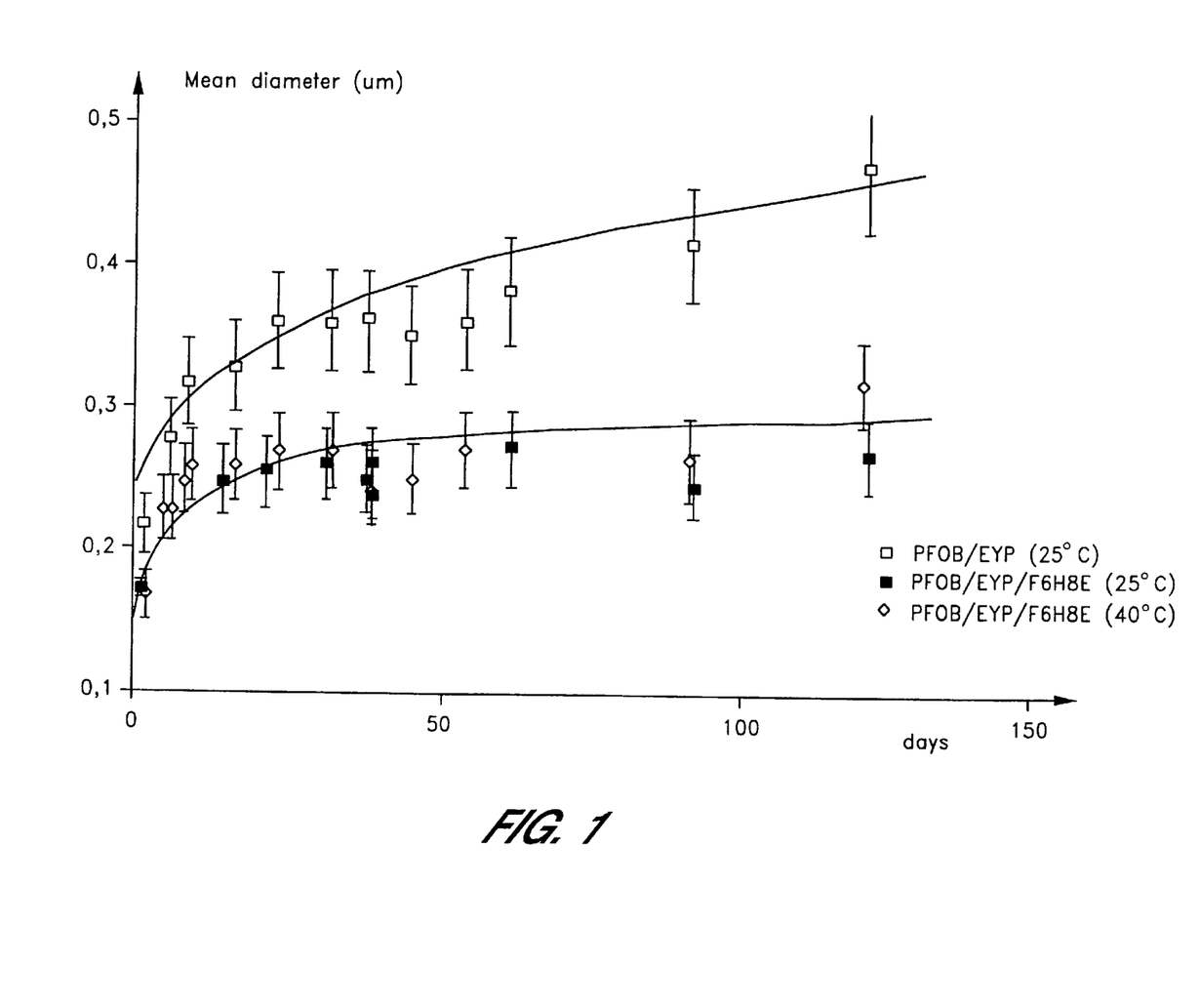
FIG. 1 represents the change in the average diameters (in μm) of particles of perfluorooctyl bromide (PFOB; perflubron®) emulsions conforming to the invention and comprising the fluorophilic/lipophilic compound $C_6F_{13}CH=CHC_8H_{17}$:F6H8E, and of particles of a reference emulsion, prepared without F6H8E, as a function of time (in days) during aging, at 25° C. or 40° C.
Figure 2:
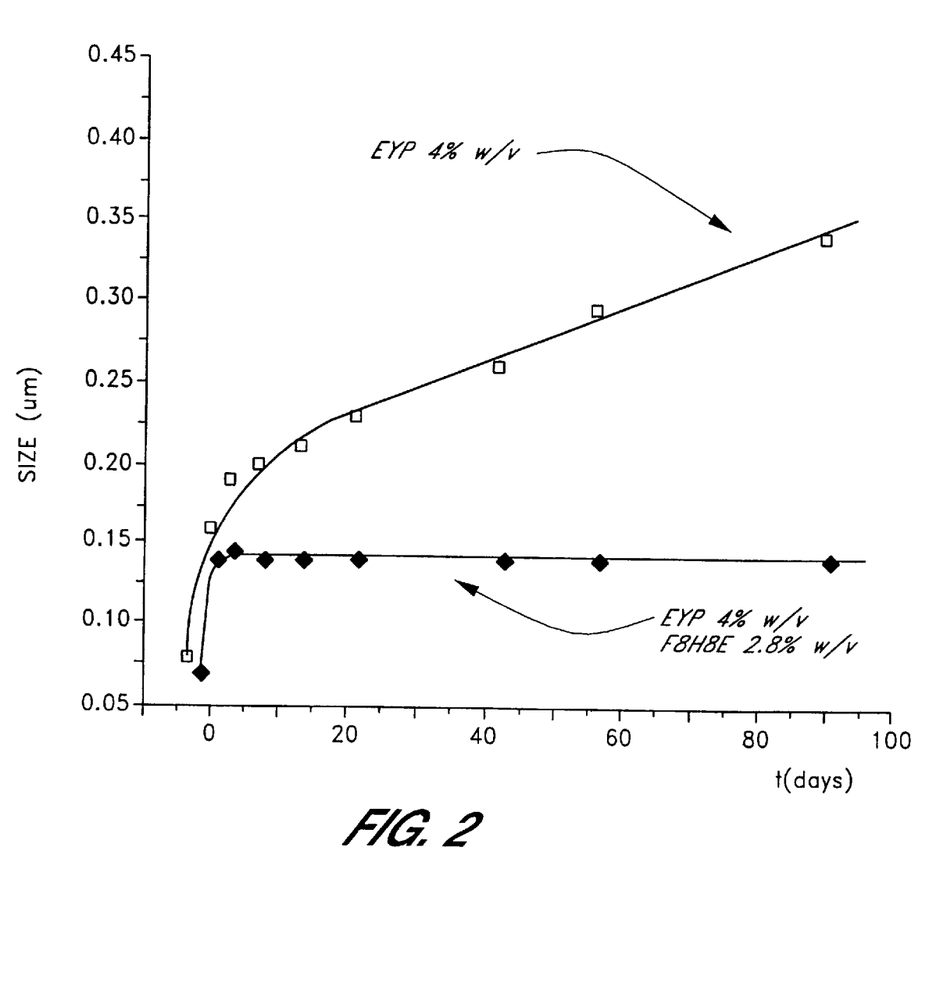
FIG. 2 represents the change in the average diameters (in μm) of particles of Perflubrons emulsions of the invention comprising the fluorophilic/lipophilic compound $C_8F_{17}CH=CHC_8H_{17}$:F8H8E, and of particles of a reference emulsion, prepared without F8H8E, as a function of time (in days) during aging at 40° C.
Figure 3:
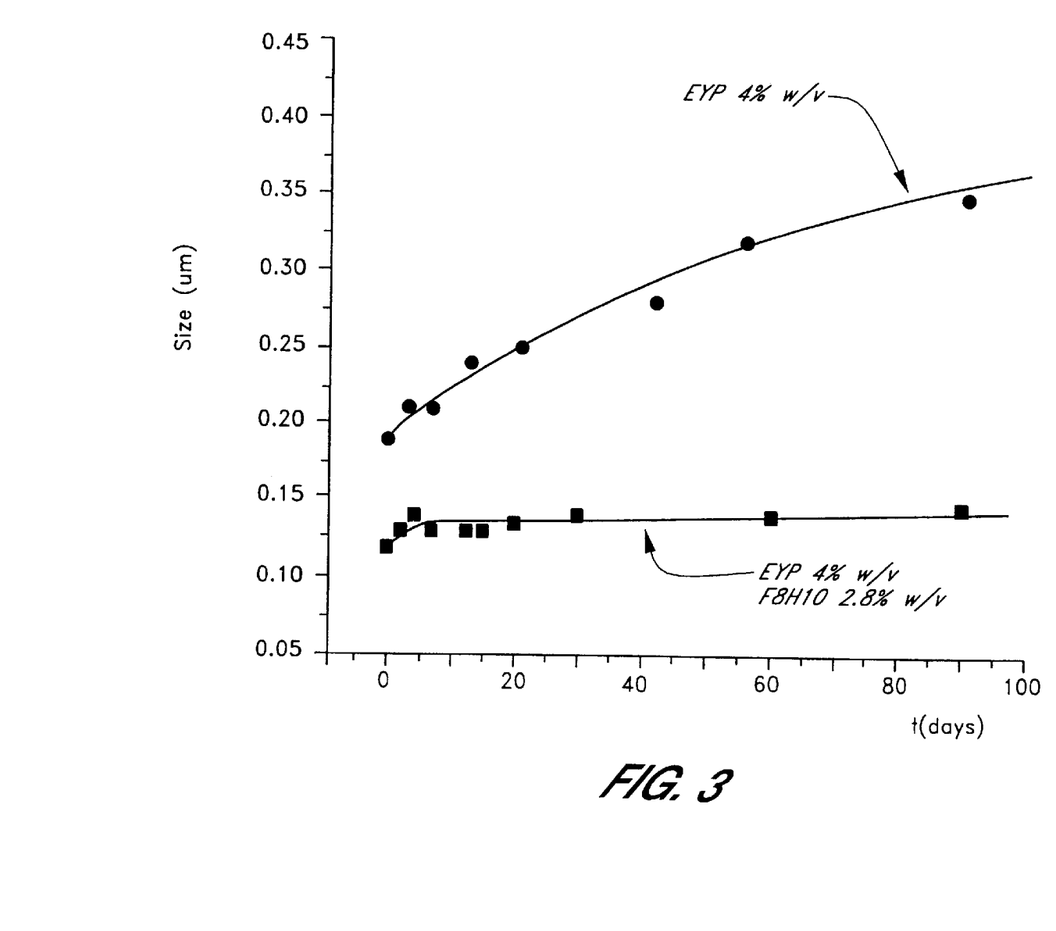
FIG. 3 represents the change in the average diameters (in μm) of particles of perfluorooctyl bromide emulsions of the invention comprising the fluorophilic/lipophilic compound F8H10, and of particles of a reference emulsion, as a function of time (in days) during aging at 40° C.
Figure 7:
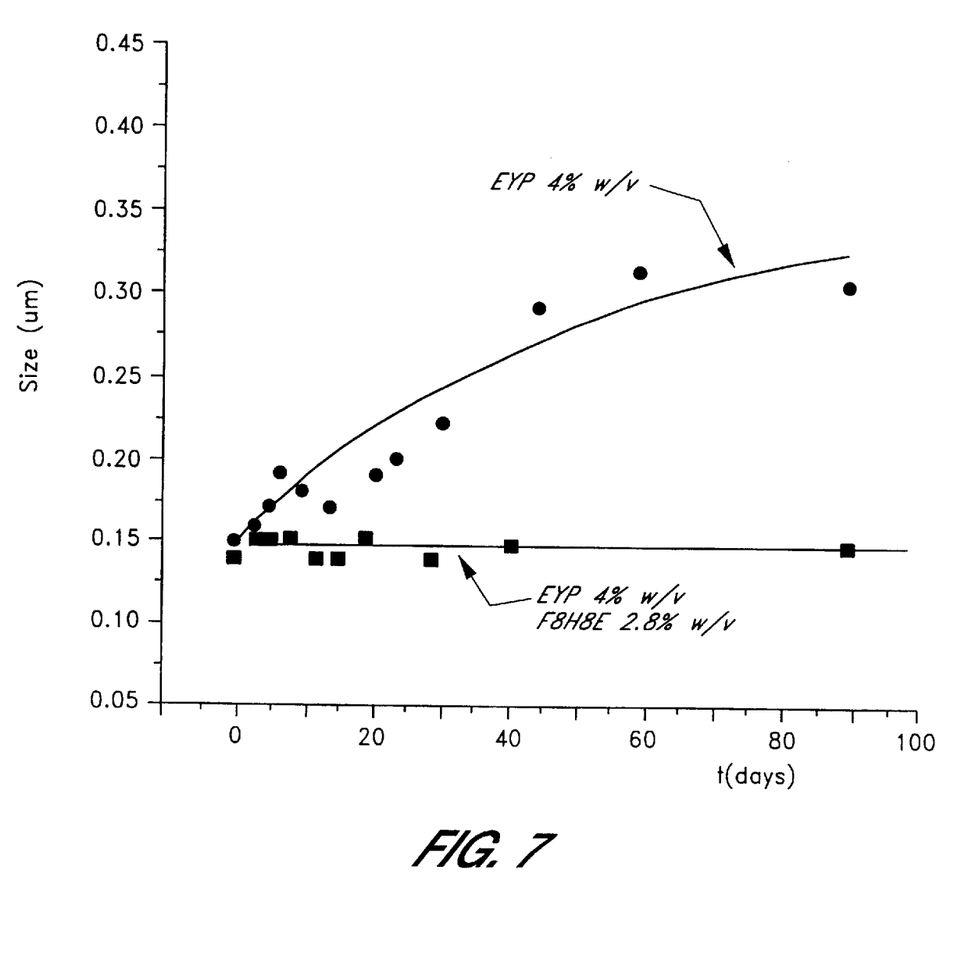
FIG. 7 represents the change in the average diameters (in μm) of particles of 1,2-bis-(F-butyl)ethene (F-44E) emulsions of the invention comprising the fluorophilic/lipophilic compound $C_8F_{17}CH=CHC_8H_{17}$ (F8H8E), and of particles of a reference emulsion prepared without F8H8E, as a function of time (in days) during aging at 40° C.
Figure 8:
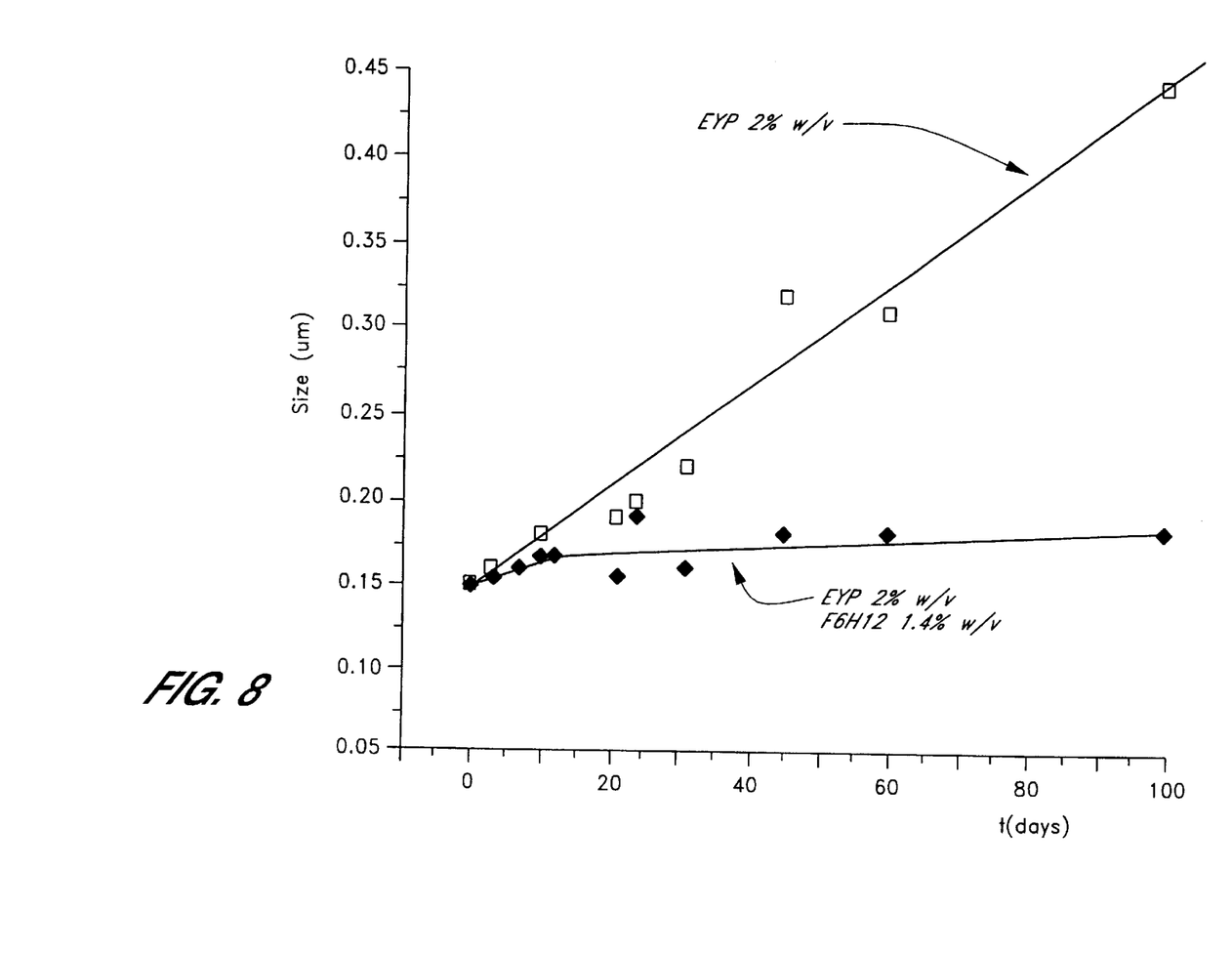
FIG. 8 represents the change in the average diameters (in μm) of particles of perflubron® emulsions of the invention comprising the fluorophilic/lipophilic compound $C_6F_{13}C_{12}H_{25}$ (F6H12), and of particles of a reference emulsion prepared without F6H12, as a function of time (in days) during aging at 40° C.

The fluorophilic/hydrophilic compounds used in the invention achieve emulsion particle size stability when added to 90/4% w/v PFOB/EYP emulsion. These compounds retain particle size at 0.13 µm after sterilization, and maintain this particle size for 3 months at 40° C. (FIGS. 2, 3, and Table II). By comparison, the reference emulsion containing only PFOB/EYP grows from 0.15 µm after sterilization to 0.32 µm after 3 months at 40° C. The same phenomenon of stabilization is observed when the compounds used in the present invention are added to F-44E/EYP 90/4% w/v emulsions; the particle size stays at 0.14 µm after sterilization, and after 3 months at 40° C. By comparison, the particle size diameter in the reference emulsion increases from 0.15 µm to 0.32 µm (FIGS. 7, 8, Table III).

Figure 4:
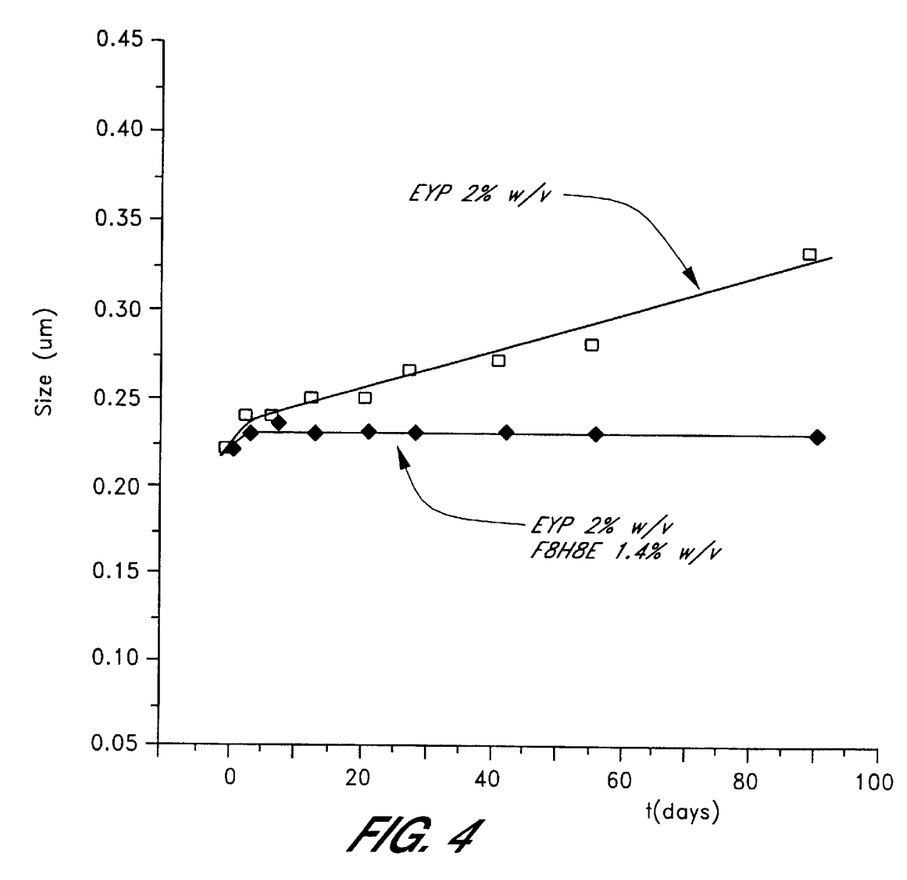
FIG. 4 represents the change in the average diameters (in μm) of particles of perfluorooctyl bromide (perflubron) emulsions of the invention comprising the fluorophilic/lipophilic compound $C_8F_{17}CH=CHC_8H_{17}$(F8H8E), and particles of a reference emulsion prepared without F8H8E, as a function of time (in days) during aging at 40° C.
Figure 5:
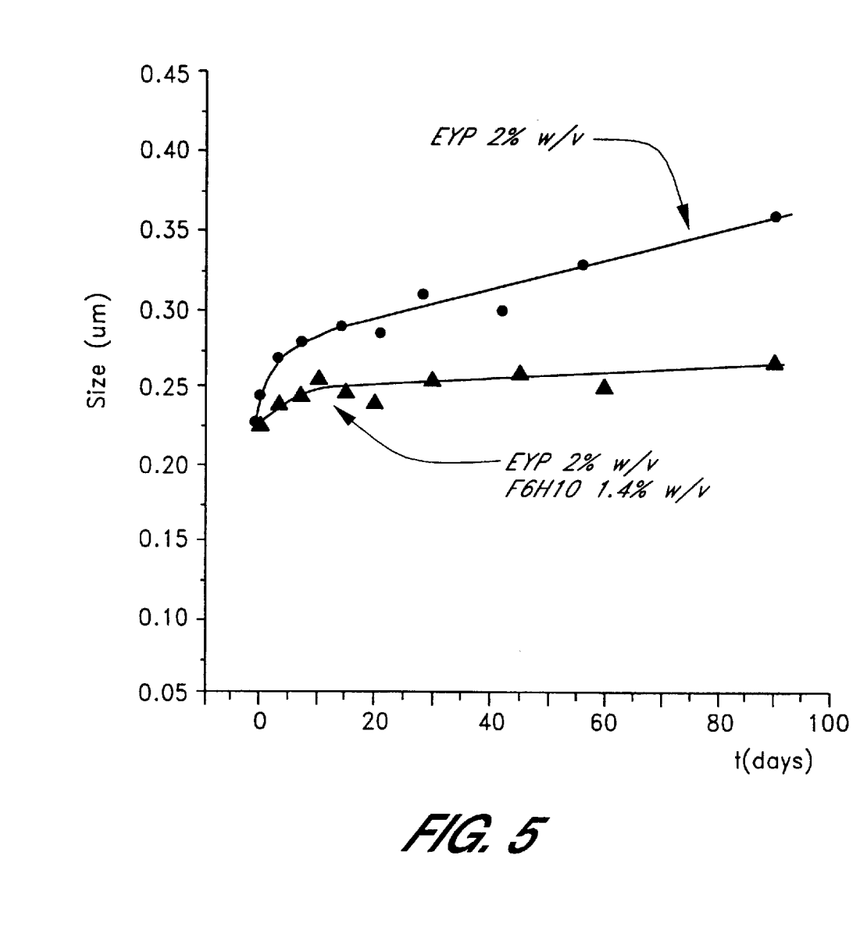
FIG. 5 represents the change in the average diameter (in μm) of particles of perfluorooctyl bromide (perflubron™) emulsions of the invention comprising the fluorophilic/lipophilic compound $C_6F_{13}C_{10}H_{21}$ (F6H10), and of particles of a reference emulsion prepared without F8H10, as a function of time (in days) during aging at 40° C.
Figure 6:
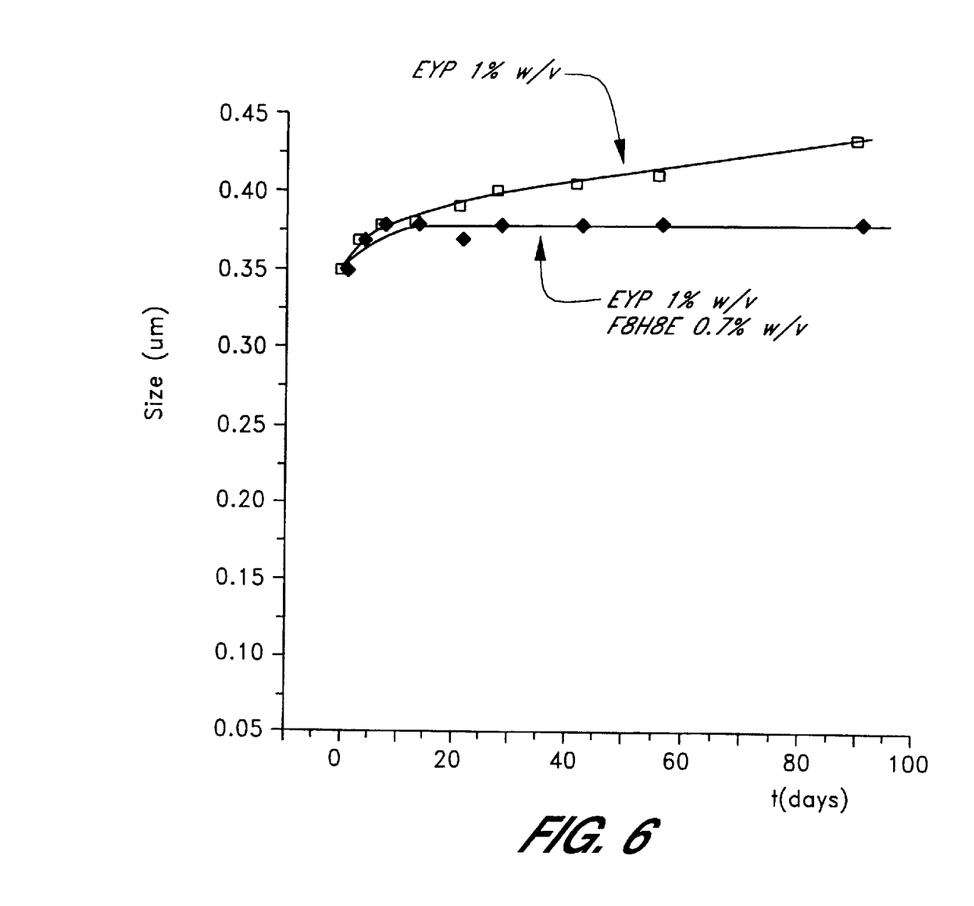
FIG. 6 represents the change in the actual diameters (in μm) of particles of perfluorooctyl bromide (perflubron™) emulsions of the invention comprising the fluorophilic/lipophilic compound $C_8F_{17}CH=CHC_8H_{17}$ (F8H8E) in 0.7% w/v amount, and of particles of a reference emulsion prepared without F8H8E, as a function of time (days) during aging at 40° C.

The fluorophilic/hydrophilic compounds used in the invention also allow one to control emulsion particle size and particle size stability. The adjustment of particle size in obtained by adjusting, for a given amount of fluorocarbon, the total amount of the mixture of fluorophilic/hydrophilic compound and lecithin; for example, the particle size is about 0.23 µm when a 90% w/v emulsion of perfluorooctyl bromide is stabilized using a mixture consisting of 2% w/v of EYP and 1.4% w/v of F8H8E (FIG. 4); or the particle size is about 0.38 µm when the 90% w/v emulsion of perfluorooctyl bromide is stabilized using a mixture consisting of 1% w/v of EYP and 0.7% w/v of F8H8E (FIG. 6); or the particle size is about 1.5 µm when a 90% w/v emulsion of perfluorooctyl bromide is stabilized using a mixture consisting of 0.2% w/v of EYP and an equimolar amount of F8H8E; or the particle size is about 2.75 µm when a 90% w/v emulsion of perfluorooctyl bromide is stabilized using a mixture consisting of 0.1% w/v EYP and an equimolar amount of F8H8E, and so forth.

The effective ratio of the amount of the fluorophilic-hydrophilic "dowel" compounds of the invention to the amount of surfactant is independent of both the nature or species of the fluorocarbon molecule and the concentration of the fluorocarbon in the emulsion. The effective dowel/surfactant ratio has been found to be in the molar ratio of between about 1/10 and 10/1, with a preferred molar ratio of 1/1. This broad range of effective dowel/surfactant molar ratios was determined in studies using several different fluorocarbon species, for example, F-decalin, perfluorooctyl bromide (Perflubrons), and F44-E, in emulsions having fluorocarbon concentrations of from about 20% w/v to 100% w/v, and containing an amount of EYP surfactant varying from about 1 to 8% w/v. This comprises a $10^{-3}$ to $10^{-4}$M concentration of the EYP surfactant, and equivalent mole concentrations of other surfactants were found to be similarly effective. The molar ratio of dowel/EYP shown to be effective in these studies was 1/5, 1/3, 1/1, 2/1 and 3/1.

Figure 9:
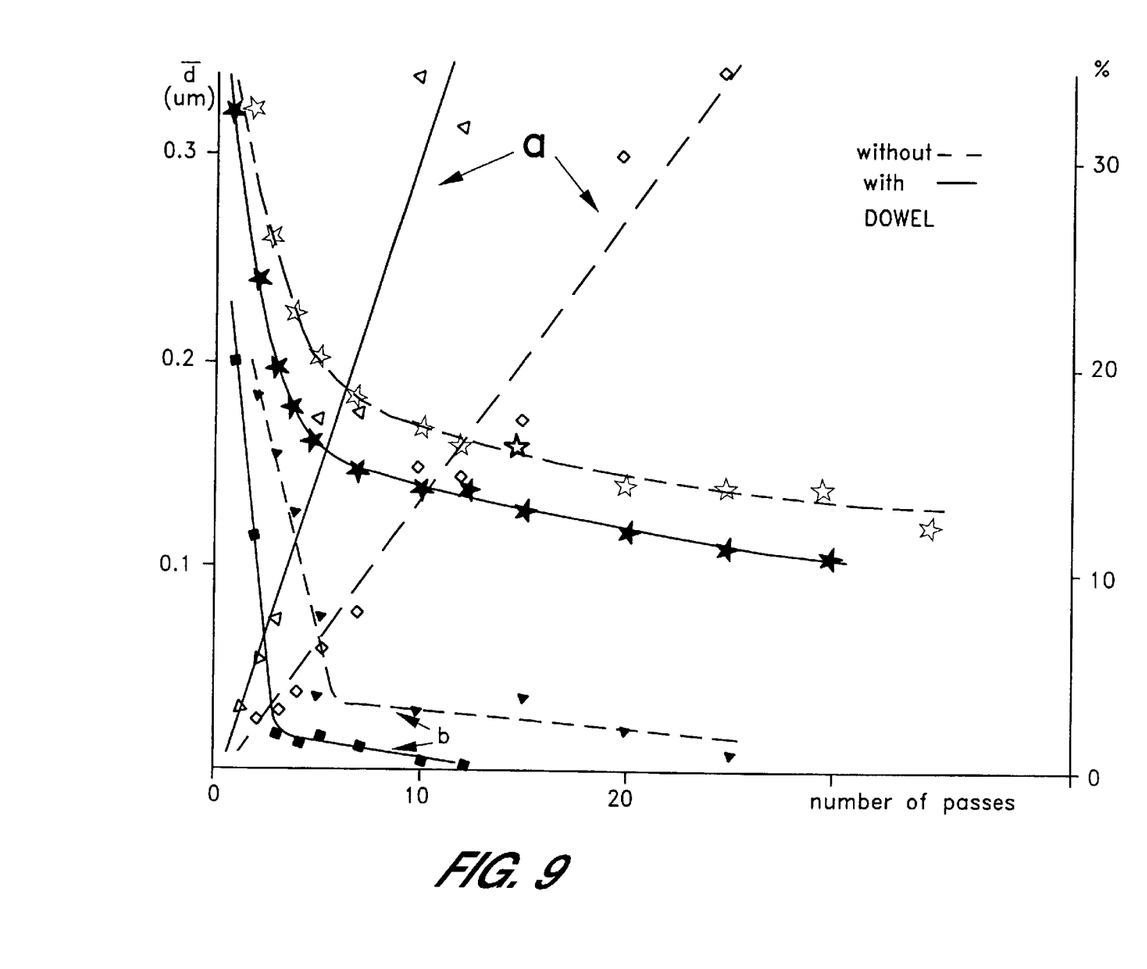
FIG. 9 demonstrates the effect of F8H8E (Dowel structure, $C_8F_{17}CH=CHC_8H_{17}$), on PFOB emulsion particle size and particle size stability, as a function of the number of passes, and the influence of adding F8H8E on the percentage of particles (a) smaller than 0.12 μm and (b) larger than 0.6 μm.

The compounds used in the methods of the invention facilitate the formation of the emulsion and lead to emulsions with fine particle size after a reduced number of passes or a reduced amount of energy. When the compound F8H8E of the invention is added to perfluorooctyl bromide/lecithin emulsion, 30% of fine particles are obtained after 10 passes. By comparison, the reference emulsion without the compounds of the invention requires 20 passes to obtain the same percentage of fine particles (FIG. 9).

The preparations of the invention, whatever their form (dispersions, emulsions or gels), can also comprise other additives, for example those generally used in emulsions, such as mineral salts, buffers, osmotic agents, oncotic agents, nutritive agents, or other ingredients that help to improve the characteristics, the stability, the efficacy and the tolerance of the emulsions.

The preparations of the invention can be used in the pharmaceutical field as medicaments in the form of emulsions or dispersions administrable, for example, orally or through the trachea, or by injection into the blood stream or into other cavities or organs of the body.

The preparations of the invention can also be used in pharmacy, cosmetics, in the veterinary or phytosanitary fields, in biology and medicine, in particular as oxygen carriers that can be employed, among other uses, as blood substitutes, or more generally for the administration of oxygen. Certain preparations of the invention can also be used as contrast agents to facilitate diagnosis, particularly by radiography, sonography or nuclear magnetic resonance imagery. The preparations, gels, emulsions or other dispersions of the invention can be used as media for treating cerebral and cardiac ischemia, for peri-operative hemodilution, for the preservation of organs, tissues, embryos, semen, as media to be used in cardiovascular therapy and surgery, for example as cardioplegic or reperfusion solutions, or in coronary angioplasty, media serving as an adjuvant in radiotherapy and chemotherapy of cancer, or as drug vehicle.

Other characteristics and advantages of the invention will be better seen in the following examples and in FIGS. 1–9. The present invention is described in detail using the following examples; however, these preferred embodiments are to be construed as merely illustrative and not limitative of the remainder of the disclosure in any way whatsoever.

In these examples, the lipophilic-fluorophilic $R_F^1$—W—$R_H^1$ compound is of the formula:

and is designated hereinafter generally as $F_{t+1}H_{y+1}E_v$, or $F_{t+1}H_{y+1}$, respectively, and specifically as:

F6H8E when t=5 and y=7, v=1;
F8H8E when t=7 and y=7, v=1;
F6H6E when t=5 and y=5, v=1;
F6H10 when t=5 and y=9, v=0.

EXAMPLES 1, 2 AND 3

STABILIZATION OF AN EMULSION OF PERFLUOROOCTYL BROMIDE/LECITHIN 90/ 4% IN WEIGHT PER VOLUME (w/v) USING A COMPOUND $R_FWR_H$.

Reference emulsion A:
Emulsions of Perflubron®/lecithin (90/4% w/v)

32 g of egg-yolk lecithin and a mixture of salts whose composition is shown in detail in Table I was dispersed with Ultra Turrax under nitrogen (24000 t/min, 10 min) in 393 mL of injectable water. Perfluorooctyl bromide (PFOB, Perflubron®) (375 mL) was added slowly to this dispersion under nitrogen. The mixture was dispersed for 10 mn at 30–40° C. The coarse emulsion obtained was passed under nitrogen through a microfluidizer (M110F). After 10 passes under a pressure of 12000 psi in the chambers cooled to 35° C., the emulsion was recovered, filled in flasks then sterilized at 121° C. for 15 mn. The ageing was monitored at 5,25 and 40° C. (Table II and FIG. 1) and the average size of the particles measured by photosedimentation.

TABLE I

Composition of reference emulsion A (for 100 mL).

| | |
|---|---|
| PFOB | 90 g |
| Lecithin | 4 g |
| NaCl | 0,3 g |
| EDTACaNa2 | 0,2 g |
| NaHPO$_4$—Na$_2$PO$_4$ | 35 mM |
| α-Tocopherol | 0,002 g |
| H$_2$O for injection | qsp 100 ml |

EXAMPLE 1

Stabilization of an emulsion of perfluorooctyl bromide/lecithin by addition of $C_6F_{13}CH=CHC_8H_{17}$ (F6H8E)

32 g of egg-yolk lecithin and a mixture of salts of the above composition (Table I) was dispersed under nitrogen using an Ultra Turrax T50 (24000 t/min, 10 min) in 379 mL of injectable water at 30–40° C. F6H8E (14.3 mL) was slowly added to this dispersion, which was stirred for 2 min. Perfluorooctyl bromide (375 mL) was then slowly added. The whole was emulsified for 10 min at 24000 t/min at 30–40° C. The coarse emulsion obtained was run under nitrogen through the microfluidizer and after 10 passes (12000 psi, 35° C.) the emulsion was filled in vials, sterilized and stored at 5,25 and 40° C. (Table II and FIG. 1).

The composition of this emulsion was the same as above but for the presence of F6H8E (2.34 g)

EXAMPLE 2

Stabilization of the emulsion of perfluorooctyl bromide/lecithin by addition of $C_8F_{17}CH=CHC_8H_{17}$ (F8H8E)

The protocol described in example 1 was used with 377 mL of water, 16.3 mL of F8H8E and 375 mL of perfluorooctyl bromide. After microfluidization the emulsion was sterilized and stored at 40° C. (Table II and FIG. 2).

EXAMPLE 3

Stabilization of an emulsion of perfluorooctyl bromide/lecithin by addition of $C_8F_{17}C_{10}H_{21}$ (F8H10)

The protocol described in example 1 and 2 was used with 377 mL of water, 22.4 g of F8H10 and 375 mL of perfluorooctyl bromide. After microfluidization the emulsion was sterilized and stored at 40° C. (Table II and FIG. 3).

EXAMPLES 4 AND 5

STABILIZATION OF AN EMULSION OF PERFLUOROOCTYL BROMIDE/LECITHIN 90/ 2% IN WEIGHT PER VOLUME (w/v) USING A COMPOUND $R_FWR_H$.

Reference emulsion B : Emulsions of perfluorooctyl bromide /lecithin (96/2% w/v)

The same protocol described in the example of Reference A was used but for 16 g of egg-yolk lecithin. The aging was monitored at 40° C. (Table II and FIG. 4).

EXAMPLE 4

Stabilization of an emulsion of perfluorooctyl bromide/lecithin by addition of $C_8F_{17}CH=CHC_8H_{17}$ (F8H8E)

The protocol described in example 1 was used with 385 mL of water, 8.38 mL of F8H8E, 16 g of lecithin and 375 mL of perfluorooctyl bromide. After microfluidization, the emulsion was sterilized and stored at 40° C. (Table II and FIG. 4). EXAMPLE 5

Stabilization of the emulsion of perfluorooctyl bromide/lecithin by addition of $C_6F_{13}C_{10}H_{21}$ (F6H10)

The protocol described in example 1 was used with 392 mL of water, 7,53 mL of F6H10, 32 g of lecithin and 375 mL of perfluorooctyl bromide. After microfluidization the emulsion was sterilized and stored at 40° C. (Table II and FIG. 5).

EXAMPLE 6

STABILIZATION OF AN EMULSION OF PERFLUOROOCTYL BROMIDE (PFOB)/ LECITHIN 90/1% IN WEIGHT PER VOLUME (w/v) USING A COMPOUND $R_FWR_H$.

Reference emulsion C: Emulsions of perfluorooctyl bromide/lecithin (90/1% w/v)

The same protocol described in example of reference A was used but for 8 g of egg-yolk lecithin. The aging was monitored at 40° C. (Table II and FIG. 6 ) and the average size of the particles was measured by photosedimentation.

EXAMPLE 6

Stabilization of an emulsion of perfluorooctyl bromide/lecithin/water by addition of $C_8F_{17}CH=CHC_8H_{17}$ (F8H8E)

The protocol described in example 1 was used with 382 mL of water, 4,19 mL of F8H8E, 8 g of lecithin and 375 mL of perfluorooctyl bromide. After microfluidization the emulsion was sterilized and stored at 40° C. (Table II and FIG. 6).

TABLE II

Comparison of stability over time, at 40° C., of perfluorooctyl bromide/lecithin 90/4% w/v of various formulations containing $R_FWR_H$ and without [as measured by mean diameter, d, of emulsion particles in μm].

| Formulation of emulsions PFOB/lecithin/$R_FWR_H$ % w/v | | at preparation | after sterilization | after 12 days at 40° C. | after 3 months at 40° C. |
|---|---|---|---|---|---|
| Ref A: 90/4/0 | | 0.14 | 0.15 | 0.17 | 0.32 |
| Example 1: 90/4/2.34 | (F6H8E) | 0.12 | 0.13 | 0.15 | 0.15 |
| Example 2: 90/4/2.85 | (F8H8E) | 0.10 | 0.13 | 0.13 | 0.13 |
| Example 3: 90/4/2.8 | (F8H10) | 0.11 | 0.13 | 0.14 | 0.14 |
| Ref B: 90/2/0 | | 0.13 | 0.24 | 0.29 | 0.36 |
| Example 4: 90/2/1.4 | (F8H8E) | 0.20 | 0.25 | 0.28 | 0.28 |
| Example 5: 90/2/1.4 | (F6H10) | 0.17 | 0.22 | 0.25 | 0.25 |
| Ref C: 90/1/0 | | 0.20 | 0.40 | 0.42 | 0.47 |
| Example 6: 90/1/0.7 | (F8H8E) | 0.20 | 0.40 | 0.41 | 0.40 |

It is seen that the addition of small quantities of compounds of the type $R_F$—W—$R_H$ to the formula of concentrated fluorocarbon emulsions results in strong stabilization. The size of the fluorocarbon droplets increases significantly more slowly (compare in particular the average diameters of the droplets after 12 days and 3 months) in the emulsions containing these mixed hydrocarbon/fluorocarbon compounds than in the reference emulsions which contain none. These results are also illustrated in FIGS. 1, 2, 3, 4 and 5. It is also noteworthly from example 4, 5 and 6 that the average particle size can be adjusted, and remains constant over a significant period of time, by adjusting the amount of EYP+mixed hydrocarbon/fluorocarbon compound present in the formulation.

EXAMPLES 7 and 8

STABILIZATION OF AN EMULSION OF 1,2-BIS (F-BUTYL)ETHENE/LECITHIN 90/4% IN WEIGHT PER VOLUME (w/v) USING A COMPOUND $R_FWR_H$.

Reference D: Emulsions of 1.2-bis(F-butyl)ethene (F-44E)/lecithin/(90/4% w/v)

4 g of egg-yolk lecithin and a mixture of salts whose composition was shown below are dispersed with Ultra Turrax under nitrogen (24000 t/min, 10 min) in 41.16 mL of injectable water. 1,2-Perfluorobutylethene (F-44E) (54 mL) was added slowly to this dispersion under nitrogen. The mixture is dispersed for 10 mn at 30–40° C.

The coarse emulsion obtained is transferred under nitrogen into a microfluidizer (M110F). After 12 passes under a pressure of 12000 psi in the chambers cooled to 35° C., the emulsion was recovered, placed in flasks, then sterilized at 121° C. for 15 min. The aging was monitored at 40° C. (Table III and FIG. 7) and the average size of the particles is measured by photosedimentation. Composition of the reference emulsion (for 100 mL).

| Composition | Grams |
|---|---|
| F-44E | 90 |
| Lecithin | 4 |
| $NaHPO_4$—$Na_2PO_4$ | 54 mM—15.3 mM |
| $H_2O$ for injection | 41.2 |

EXAMPLE 7

Stabilization of an emulsion of 1,2-bis(F-butyl) ethene (F-44E)/lecithin by addition of $C_8F_{17}CH=CHC_8H_{17}$ (F8H8E)

4 g of egg-yolk lecithin and a mixture of salts of the above composition were dispersed in 39.94 mL of injectable water at 30–40° C. F8H8E (2.05 mL) was slowly added to this dispersion, which is stirred for 2 min (8000 t/min). 1,2-bis (F-butyl)ethene (F-44E) (54 mL) was then slowly added to the F8H8E/lecithin mixture under nitrogen. The whole was emulsified for 10 min at 24000 t/min at 30–40° C. The coarse emulsion was transferred under nitrogen into the microfluidizer and after 12 passes (12000 psi, 35° C.) the emulsion was sterilized and stored at 40° C. (Table III and FIG. 7 ).

EXAMPLE 8

Stabilization of an emulsion of 1,2-bis (F-butyl) ethene (F-44E) /lecithin/water by addition of $C_6F_{13}C_{12}H_{25}$ (F6H12)

The protocol described in example 7 was used with 39.9 mL of water 2 mL of F6H12, 4 g of lecithin and 54 mL of perfluorooctyl bromide. After microfluidization the emulsion was sterilized and stored at 5, 25 and 40° C. (Table III and FIG. 8).

TABLE III

Comparison of stability over time, at 40° C., or 1,2-bis(F-butyl)ethene (F-44E)/lecithin 90/4% w/v containing $R_FWR_H$ and without.

| Formulation of emulsions F-44/lecithine/$R_FWR_H$ % w/v | | at preparation | after sterilization | after 12 days at 40° C. | after 3 months at 40° C. |
|---|---|---|---|---|---|
| Ref D: 90/4/0 | | 0.14 | 0.15 | 0.17 | 0.32 |
| Example 7: 90/4/2.34 | (F6H8E) | 0.13 | 0.14 | 0.13 | 0.14 |
| Example 8: 90/4/2.85 | (F8H8E) | 0.14 | 0.15 | 0.16 | |

It is seen that the addition of small quantities of compounds $R_F$—W—$R_H$ to the formula of concentrated fluorocarbon emulsions results in strong stabilization, because the size of the fluorocarbon droplets increases significantly more slowly (compare in particular the average diameters of the droplets after 12 days and 3 or 4 months) in the emulsions containing these mixed compounds than in the reference emulsion which contains none.

EXAMPLE 9

FACILITATION OF EMULSIFICATION OF PERFLUOROOCTYL BROMIDE BY ADDITION OF $C_8F_{17}CH=CHC_8H_{17}$ (F8H8E)

Reference Emulsion E: Emulsion of Perfluorooctyl bromide (90/4/% w/v)

The protocol described in Example 1 was used. The average particle size was measured during microfluidization after 1, 2, 3, 4, 5, 7 and 10 passes. The percentage of fine particles (d<0,12 μm) and of coarse particle (d>0,6 μm) was evaluated.

Results are reported in FIG. 9.

EXAMPLE 9

Effect of the addition of $C_8F_{17}CH{=}CHC_8H_{17}$ (F8H8E) on the emulsification of perfluorooctyl bromide.

The same protocol as for reference emulsion E was used but for the addition of (F8H8E) as described in example 2. Results are shown in FIG. 9.

It is seen that upon the addition of small amounts of the mixed fluorocarbon-hydrocarbon amphiphilic compounds small emulsion droplets (smaller than 0.12 μm) are formed more rapidly. The number of droplets larger than 0.6 μm is reduced faster and lower average particle size is attained faster.

The invention may be embodied in other specific forms without departing from its spirit or essential characteristics. The described embodiments are to be considered in all respects only as illustrative and not restrictive, and the scope of the invention is, therefore, indicated by the appended claims rather than by the foregoing description. All modifications which come within the meaning and range of the lawful equivalency of the claims are to be embraced within their scope.

What is claimed is:

1. A method for controlling emulsion particle size and emulsion particle size stability, the method comprising:

forming a mixture by combining an emulsion particle size stabilizing effective amount of a lipophilic-fluorophilic compound, a surfactant, an aqueous continuous phase and perfluorooctyl bromide, said lipophilic-fluorophilic compound of the formula:

or wherein:
t=2 to 11;
y=0 to 6;
v=1 to 15; and emulsifying the mixture.

2. The method of claim 1, wherein said surfactant is egg yolk phospholipid (denoted as EYP).

3. The method of claim 1, wherein the lipophilic-fluorophilic compound is selected from the group consisting of:

$CF_3(CF_2)_5$—CH=CH—$(CH_2)_7$—$CH_3$ (denoted as F6H8E);

$CF_3(CF_2)_7$—CH=CH—$(CH_2)_7$—$CH_3$ (denoted as F8H8E);

$CF_3(CF_2)_5$—CH=CH—$(CH_2)_5$—$CH_3$ (denoted as F6H6E);

$CF_3(CF_2)_5$—$(CH_2)_9$—$CH_3$ (denoted as F6H10);

$CF_3(CF_2)_7$—$(CH_2)_9$—$CH_3$ (denoted as F8H10); and $CF_3(CF_2)_5$—$(CH_2)_{11}$—$CH_3$ (denoted as F6H 12).

4. The method of claim 3, wherein said perfluorooctyl bromide is present in 10–130% w/v, said surfactant is present in 0.1–10% w/v and said lipophilic-fluorophilic compound is selected from the group consisting of F6H8E, F8H8E, F6H6E, F6H12, F6H10 and F8H10.

5. The method of claim 4, wherein said perfluorooctyl bromide is present in 50–100% w/v, said surfactant is egg yolk phospholipid (denoted as EYP) and is present in 0.1–5% w/v.

6. The method of claim 5, wherein said perfluorooctyl bromide is present in 50–70% w/v, said surfactant is EYP and is present in 0.1–5% w/v and said lipophilic-fluorophilic compound is F6H10.

7. The method of claim 1, wherein said perfluorooctyl bromide is present in 60% w/v, said surfactant is egg yolk phospholipid (denoted as EYP) and is present in 0.1% w/v and said lipophilic-fluorophilic compound is $CF_3(CF_2)_5$—$(CH_2)_9$—$CH_3$ (denoted as F6H10) and is present in 0.1–0.2% w/v.

8. The method of claim 1, wherein said surfactant is egg yolk phospholipid (denoted as EYP) and wherein the ratio of said EYP to said lipophilic-fluorophilic compound is between 1:10–10:1.

9. The method of claim 1, wherein said surfactant is egg yolk Phospholipid (denoted as EYP) and wherein the ratio of said EYP to said lipophilic-fluorophilic compound is 1:1.

10. The method of claim 1, further including dispersing said mixture containing the lipophilic-fluorophilic compound, the surfactant, the aqueous continuous phase and perfluorooctyl bromide at a temperature of 30–40° C.

* * * * *